(12) United States Patent
Carter et al.

(10) Patent No.: US 9,008,787 B2
(45) Date of Patent: Apr. 14, 2015

(54) ACTIVE ELECTRODE STATE CONTROL SYSTEM

(75) Inventors: Paul M. Carter, Wesr Pennant Hills (AU); Torsten Lehmann, Earlwood (AU); Christopher van den Honert, Aurora, CO (US); Ibrahim Ibrahim, North Ryde (AU); Tony M. Nygard, Terrigal (AU)

(73) Assignee: Cochlear Limited, Macquarie University, NSW (AU)

( * ) Notice: Subject to any disclaimer, the term of this patent is extended or adjusted under 35 U.S.C. 154(b) by 813 days.

(21) Appl. No.: 12/771,917

(22) Filed: Apr. 30, 2010
(Under 37 CFR 1.47)

(65) Prior Publication Data

US 2011/0125217 A1  May 26, 2011

Related U.S. Application Data

(63) Continuation-in-part of application No. 12/682,780, filed as application No. PCT/AU2008/001506 on Oct. 10, 2008, now Pat. No. 8,588,928.

(30) Foreign Application Priority Data

Oct. 12, 2007 (AU) ................................ 2007905586
Apr. 30, 2009 (AU) ................................ 2009901913

(51) Int. Cl.
*A61N 1/36* (2006.01)
(52) U.S. Cl.
CPC .................................. *A61N 1/36032* (2013.01)
(58) Field of Classification Search
None
See application file for complete search history.

(56) References Cited

U.S. PATENT DOCUMENTS

| 4,141,359 | A | 2/1979 | Jacobsen et al. |
| 4,343,312 | A | 8/1982 | Cals et al. |
| 4,532,930 | A | 8/1985 | Crosby et al. |

(Continued)

FOREIGN PATENT DOCUMENTS

| DE | 102004059973 A1 | 6/2006 |
| EP | 0241101 A1 | 10/1987 |

(Continued)

OTHER PUBLICATIONS

International Search Report for PCT/AU2008/001506, dated Nov. 25, 2008.

(Continued)

*Primary Examiner* — Kennedy Schaetzle
(74) *Attorney, Agent, or Firm* — Lowe Hauptman & Ham, LLP

(57) ABSTRACT

A method and system for charge imbalance compensation in a stimulating medical device is provided. The stimulating medical device includes at least one electrode contact configured for providing stimulation to a recipient. A charge imbalance compensation system in the stimulating medical device measures any residual charge remaining on the electrode contact that may result from an imbalance in the applied stimulation. If the measured residual charge exceeds a threshold, the charge imbalance compensation system causes a compensator current to be applied to reduce the residual charge. This residual charge may be measured by measuring a potential difference between the electrode contact and a reference electrode; or, by measuring a potential difference across a capacitor in-series with the electrode contact.

23 Claims, 13 Drawing Sheets

(56) References Cited

U.S. PATENT DOCUMENTS

| | | | |
|---|---|---|---|
| 4,811,738 A | 3/1989 | Economides et al. | |
| 5,324,316 A | 6/1994 | Schulman et al. | |
| 5,603,725 A | 2/1997 | Schaldach | |
| 5,674,264 A | 10/1997 | Carter et al. | |
| 6,219,580 B1 | 4/2001 | Faltys et al. | |
| 6,600,955 B1 | 7/2003 | Zierhofer | |
| 6,895,278 B1 * | 5/2005 | Gordon | 607/40 |
| 7,277,751 B2 | 10/2007 | Dupelle et al. | |
| 2004/0267344 A1 | 12/2004 | Stett et al. | |
| 2006/0224199 A1 | 10/2006 | Zeijlemaker | |
| 2008/0015641 A1 | 1/2008 | Armstrong et al. | |

FOREIGN PATENT DOCUMENTS

| | | |
|---|---|---|
| EP | 1384434 A1 | 1/2004 |
| WO | 9721324 A1 | 6/1997 |

OTHER PUBLICATIONS

Written Opinion. PCT/AU2008/001506. Mailed Nov. 25, 2008.

* cited by examiner

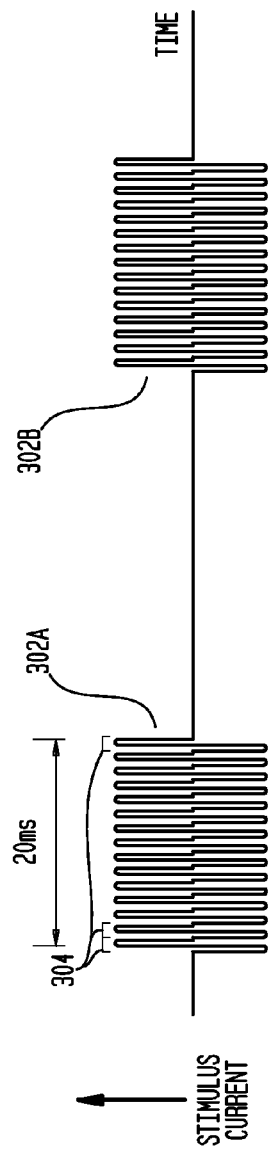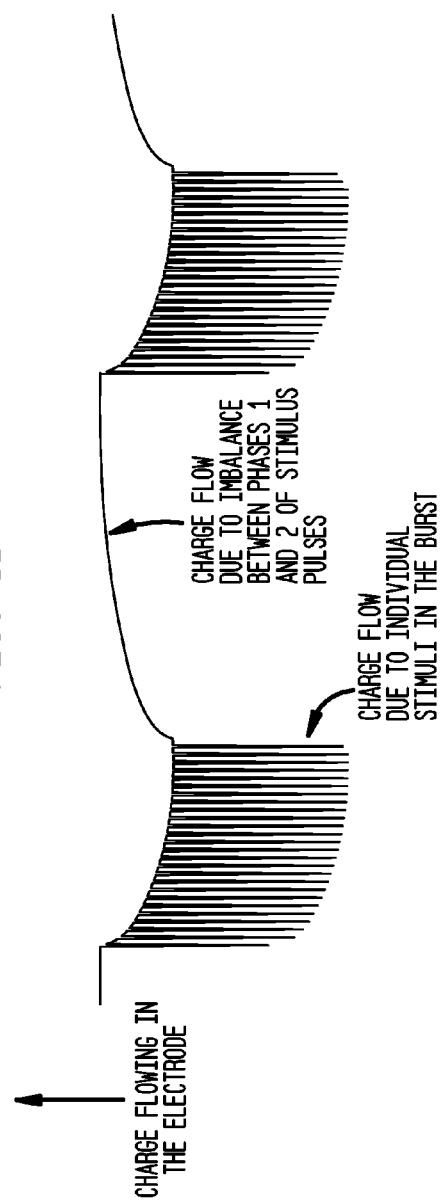

ACTIVE ELECTRODE STATE CONTROL SYSTEM

CROSS-REFERENCE TO RELATED APPLICATIONS

This application is a continuation-in-part of U.S. patent application Ser. No. 12/682,780 entitled "Active Electrode State Control System," filed Apr. 12, 2010, now U.S. Pat. No. 8,588,928, which claims priority to PCT Application No. PCT/AU2008/001506 filed Oct. 10, 2008 and Australian Provisional Application No. 2007905586 filed Oct. 12, 2007. The content of these applications are hereby incorporated by reference herein.

This application also claims priority to Australian Provisional Application No. 2009901913 entitled "Residual Charge Control for Electrical Stimulators," filed on 30 Apr. 2009, the contents of which are hereby incorporated by reference herein.

BACKGROUND

1. Field of the Invention

The present invention relates generally to electrical stimulation systems, and more particularly, to the control of charge imbalances in electrical stimulation systems.

2. Related Art

Electronic devices implanted within the body in order to stimulate nerve tissue (e.g. cochlear implants) for perceptual or functional purposes generally use platinum electrodes as the interface between the electronics and the body tissue. In general terms, such electrodes are selectively driven with a current in order to evoke a perception (for example sound) or a function (for example a limb movement) in the user. In application, a stimulating current is applied to the implanted electrodes. This current passes through the implant recipient's tissue and the nerve cell, and returns to the implant. At the surface of the electrodes, chemical reactions may take place, changing the electron current in the electronics to an ion current in the tissue. Further, a charge remains on the electrode surface, causing an increase in voltage across the electrode-tissue interface. Under normal operation of the interface, these chemical reactions are reversible when the current direction is changed, leaving a neutral interface.

It is usual for the stimuli to be structured as biphasic pulses, in such a way that there is no net charge delivered to the tissue. If, however, the current is allowed to flow in one direction for too long, toxic products can escape the interface and damage or destroy the surrounding tissue. Likewise, if the voltage across the interface is allowed to remain elevated for too long, toxic species are irreversibly generated at the interface. To ensure that stimulation is safe, and that no toxic species escape the interface, it must be ensured that the DC and low-frequency (LF) states of the electrodes, i.e. the DC/LF interface voltages and the DC/LF interface currents, remain within certain bounds. The usual target values are a factor of hundreds of milli-volts, or some tens of nano-amperes (for typical cochlear implant electrode areas of about 0.25 $mm^2$) The United State's Food and Drug Administration (FDA) requires that the magnitude of the current through an electrode be below 100 nA measured over any 1 milli-second period.

The use of charge-neutral pulses ensures, in principle, that the FDA requirement for the DC/LF current is met. In practice, however there will be a small error in the generated stimulation current. This requires a second measure to be taken to ensure low levels of DC/LF current are maintained at all times. This is particularly an issue when high stimulation rates and high current levels are used. Further, if the stimulation current source goes out of compliance, then significant charge errors can occur. A number of approaches are currently employed to control the interface voltage and current.

One approach is to use DC blocking capacitors for each electrode to ensure zero DC currents through the electrodes. This DC blocking capacitor is disposed in the stimulation current path. A capacitor may also be disposed in the stimulation current path of the monopolar return electrode in implementations employing monopolar stimulation. In order for this approach to be effective, it is necessary to provide a capacitor with relatively high capacitance, in the hundreds of nano-farad range, for each electrode. With current capacitor technology, this cannot be fabricated in an integrated circuit, and so discrete components are used, which may increase the required space for the implant. This type of approach is discussed in, for example, U.S. Pat. No. 5,324,316 to Schulman et al, U.S. Pat. No. 6,600,955 to Zierhofer et al, and U.S. Pat. No. 6,219,580 to Faltys et al.

Another approach is to use periodic short-circuiting of all electrodes to ensure that the DC/LF electrode voltage does not drift out of the safe window. This typically employs using a shorting switch for each electrode, and periodically closing the switches thereby connecting all electrodes to ground. In some implementations (e.g., monpolar stimulation), a series capacitor is used in the return electrode only. This approach allows for up-scaling of the number of electrodes. However, shorting all the electrodes requires the stimulation protocol to include an inactive period when no stimulation takes place. This approach is discussed in European Patent No. 0,241,101 to Cochlear Limited.

Another approach is to measure the differential voltage between electrodes during a dead period and adjust the duration or amplitude of the applied stimuli to compensate for the charge error. This approach is disclosed in U.S. Pat. No. 5,674,264 to Cochlear Limited.

SUMMARY

In one aspect of the present invention a method of controlling voltage in a stimulating medical device having a plurality of electrode contacts for delivering stimulation to a recipient is provided. The method comprising: measuring a residual charge associated with an electrode contact of the plurality of electrode contacts; determining if the measured residual charge exceeds a threshold; and applying a compensation current if the measured residual charge exceeds the threshold.

In another aspect of the present invention, there is provided a stimulating medical device for delivering stimulation to a recipient, the stimulating medical device comprising: at least one electrode contact configured to deliver stimulation to the recipient; a current source configured to provide a stimulation current to the at least one electrode contact; a charge imbalance compensation system configured to measure a residual charge associated with at least one of the electrode contacts; determine if the measured residual charge exceeds a threshold; and direct that a compensation current be applied if the measured residual charge exceeds the threshold.

In yet another aspect of the present invention, there is provided a system for controlling voltage in a stimulating medical device having a plurality of electrode contacts for delivering stimulation to a recipient, the system comprising: means for measuring a residual charge associated with an electrode contact of the plurality of electrode contacts; means for determining if the measured residual charge exceeds a threshold; and means for applying a compensation current if the measured residual charge exceeds the threshold.

BRIEF DESCRIPTION OF THE DRAWINGS

Embodiments of the present invention are described below with reference to the attached drawings, in which:

FIG. 3A illustrates two pulse trains of the stimulation pulses;

FIG. 3B illustrates the charge flowing into and out of electrode contact due to the pulse trains illustrated in FIG. 3A;

DETAILED DESCRIPTION

Aspects of the present invention are generally directed to a method and system for charge imbalance compensation in a stimulating medical device. The stimulating medical device includes at least two electrode contacts configured for providing stimulation to a recipient. A charge imbalance compensation system in the stimulating medical device measures any residual charge remaining on the electrode contact that may result from an imbalance in the applied stimulation. If the measured residual charge exceeds a threshold, the charge imbalance compensation system causes a compensator current to be applied to reduce the residual charge. In the below description, an embodiment will first be described that measures the residual charge by measuring a potential difference between the electrode contact and a reference electrode. This embodiment may be useful in helping improve the safety of the stimulating medical device. After which, an embodiment will be provided that measures the residual charge by measuring a potential difference across a capacitor in-series with the electrode contact. This embodiment may be useful in both improving the safety of the stimulating medical device and helping avoid unwanted percept by the recipient due to charge imbalance.

Embodiments of the present invention are described herein primarily in connection with one type of hearing prosthesis, namely a cochlear prostheses (commonly referred to as cochlear prosthetic devices, cochlear implants, cochlear devices, and the like; simply "cochlear implants" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. It would be appreciated that embodiments of the present invention may be implemented in any cochlear implant or other hearing prosthesis now known or later developed, including auditory brain stimulators, or implantable hearing prostheses that acoustically or mechanically stimulate components of the recipient's middle or inner ear.

Figure 1:
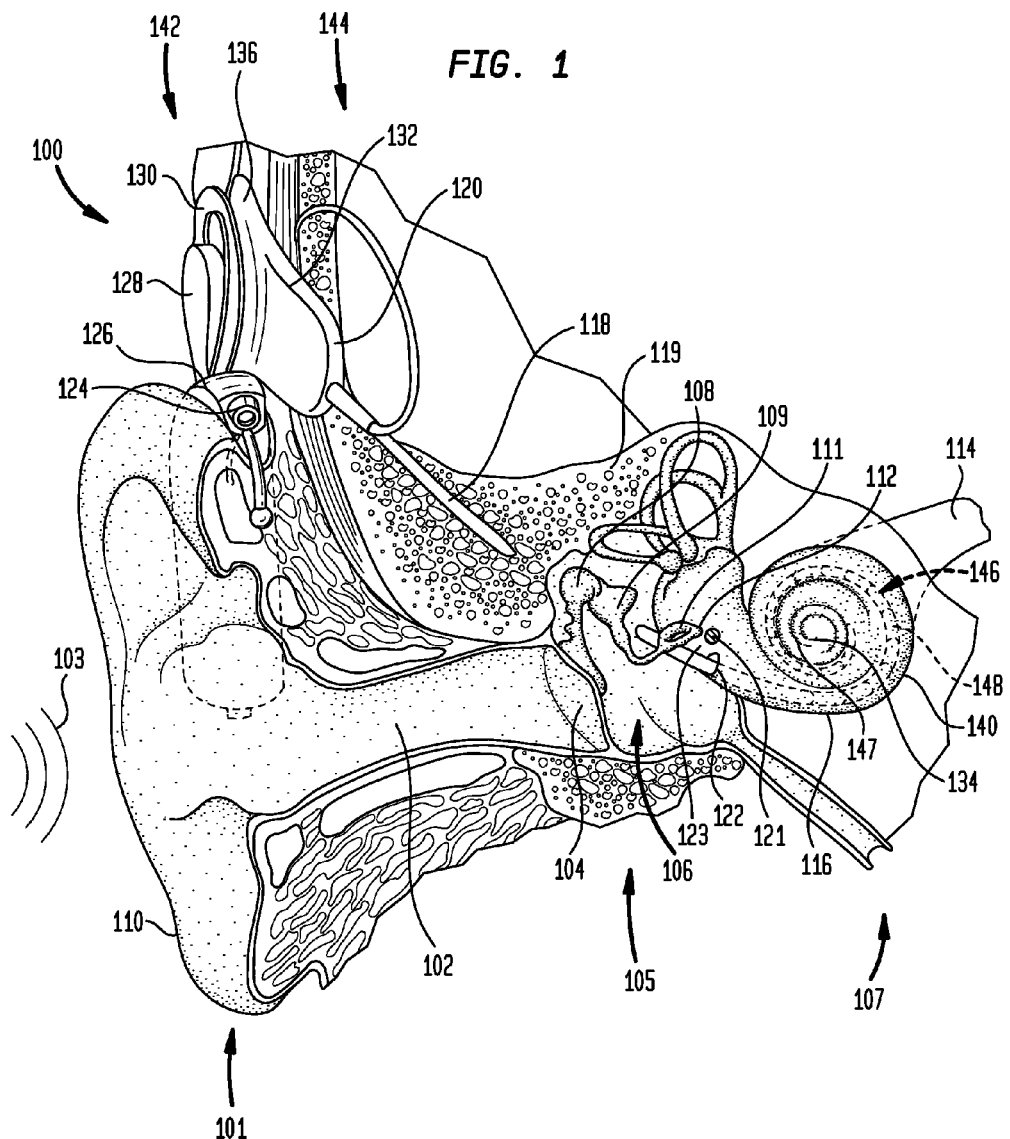
FIG. 1 is a perspective view of a cochlear implant in which embodiments of the present invention may be implemented.

FIG. 1 is perspective view of a conventional cochlear implant, referred to as cochlear implant 100 implanted in a recipient having an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

Cochlear implant 100 comprises an external component 142 which is directly or indirectly attached to the body of the recipient, and an internal component 144 which is temporarily or permanently implanted in the recipient. External component 142 typically comprises one or more sound input elements, such as microphone 124 for detecting sound, a sound processing unit 126, a power source (not shown), and an external transmitter unit 128. External transmitter unit 128 comprises an external coil 130 and, preferably, a magnet (not shown) secured directly or indirectly to external coil 130. Sound processing unit 126 processes the output of microphone 124 that is positioned, in the depicted embodiment, by auricle 110 of the recipient. Sound processing unit 126 generates encoded signals, sometimes referred to herein as encoded data signals, which are provided to external transmitter unit 128 via a cable (not shown).

Internal component 144 comprises an internal receiver unit 132, a stimulator unit 120, and an elongate electrode assembly 118. Internal receiver unit 132 comprises an internal coil 136, and preferably, a magnet (also not shown) fixed relative to the internal coil. Internal receiver unit 132 and stimulator unit 120 are hermetically sealed within a biocompatible housing, sometimes collectively referred to as a stimulator/receiver unit. The internal coil receives power and stimulation data from external coil 130, as noted above. Elongate electrode assembly 118 has a proximal end connected to stimulator unit 120, and a distal end implanted in cochlea 140. Electrode assembly 118 extends from stimulator unit 120 to cochlea 140 through mastoid bone 119. Electrode assembly 118 is implanted into cochlea 140. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrode contacts 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118. Stimulator unit 120 generates stimulation signals which are applied by electrode contacts 148 to cochlea 140, thereby stimulating auditory nerve 114.

In cochlear implant 100, external coil 130 transmits electrical signals (i.e., power and stimulation data) to internal coil 136 via a radio frequency (RF) link. Internal coil 136 is typically a wire antenna coil comprised of multiple turns of electrically insulated single-strand or multi-strand platinum or gold wire. The electrical insulation of internal coil 136 is provided by a flexible silicone molding (not shown). In use, implantable receiver unit 132 may be positioned in a recess of the temporal bone adjacent auricle 110 of the recipient.

While cochlear implant system 100 is illustrated as having external component 142, in another embodiment, one or more of the above-described components of external component 142 may be implantable. For example, in an embodiment, microphone 124 and sound processing unit 126 may be implantable, such as, for example, by encasing the microphone 124, sound processor, and a power supply in a hermetically sealed housing, such as, for example, a separate housing or the housing used for stimulator unit 120.

Figure 2A:
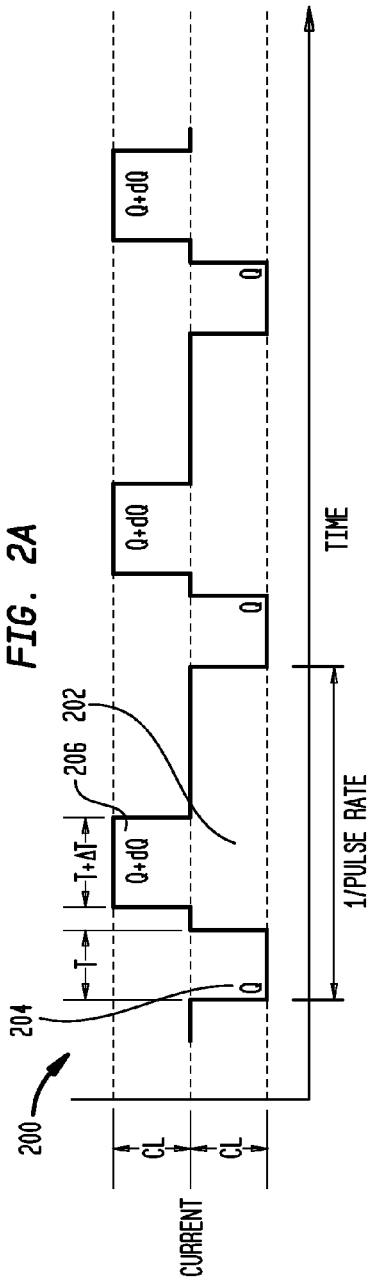
FIG. 2A illustrates a stimulation pulses showing how charge imbalances may arise.

For safety purposes, it is known that electrical stimulation delivered by electrode contacts 148 to neural structures should be charge balanced. FIG. 2A illustrates a stimulation signal showing how charge imbalances may arise and accumulate over time. As illustrated, stimulation signal 200 comprises a stream of bi-phasic pulses 202 at a pulse rate. The duration of each pulse 202 is equal to 1/(pulse rate), which may be for example, between 10 and 100 microseconds for a cochlear implant. Each bi-phasic pulse 202 comprises a negative phase 204 and a positive phase 206. As show, the negative phase 204 has a current level of −CL and a time duration of T. The negative phase 204 delivers a total charge of Q. The positive phase 206 has a current level of CL and a duration of T+ΔT. Due to the longer time duration, the positive phase 206 delivers a charge of Q+dQ, which is greater than the charge delivered during the negative phase 204. As shown, the subsequent bi-phasic pulses include the same charge imbalance.

It should be noted that FIG. 2A illustrates but one example of how a charge imbalance may arise, and in other situations the charge imbalance may arise due to other factors. For example, a charge imbalance may arise due to a difference in the current levels for each phase, or a combination of a difference in the current levels and time durations of each phase.

Charge imbalances may arise due to, for example, imperfect current sources or charge absorption at the electrode/tissue interface. Current sources have finite output impedance, particularly at higher frequencies. Because the load conditions seen by the currents sources are different between the first and positive phases of a biphasic pulse, these different load conditions may give rise to slightly different currents that flow between the two phases. Additionally, unbalanced charges may result from charge absorption at the electrode contact/tissue interface. This interface between the metal electrode contacts and the tissue is often assumed to be a pure capacitor. In practice, however, it is better modelled by a "Constant Phase Element." A further description of this model is provide in Brug et al., "The Analysis of Electrode Impedances Complicated by the Presence of a Constant Phase," J. Electroanal Chem, 176 91984, 275-295.

This interface acts as an active electrochemical cell which absorbs and releases oxygen, hydrogen, and other species onto its surface throughout the biphasic pulse. As a result, exactly equal amounts of charge can be supplied to the two phases of the biphasic pulse and a residual charge will still exist at the end. This residual charge then causes imbalance charge to flow.

Figure 2B:
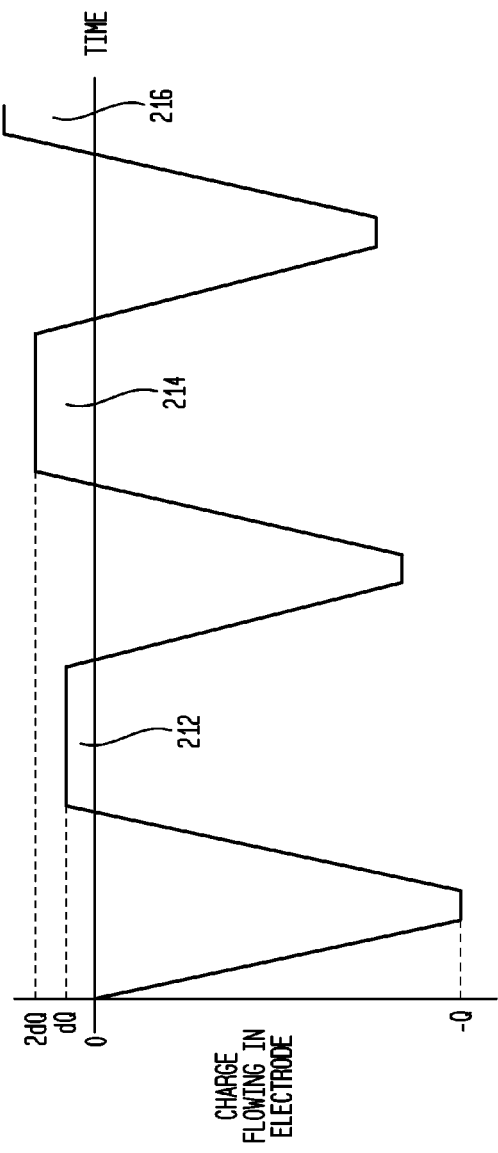
FIG. 2B illustrates how a residual charge due to charge imbalances may accumulate over time.

FIG. 2B illustrates how charge imbalances may accumulate over time. As shown, charge flowing into the electrode contact 148 during the negative phase 204 of the bi-phasic pulse 202 is equal to −Q. During the positive phase 206, a charge of Q+dQ flows into the electrode contact 148. Due to this charge imbalance, a charge of dQ 212 remains in the tissue following the first bi-phasic pulse 202. During the next pulse, an additional imbalance of dQ exists and the charge 214 remaining in the tissue grows to 2 dQ. Similarly, the charge again increases during the next pulse to a total charge 216 remaining in the tissue of 3 dQ. Thus, in the illustrated example, the charge remaining in the tissue grows by dQ during each pulse. If not corrected for, this charge remaining in the tissue will continue to grow and may result in safety and/or perceptual concerns for the recipient.

FIGS. 3A and 3B illustrate the stimulation signal 200 and the resulting charge in the tissue on a longer time scale. In FIGS. 3A and 3B it is assumed that the system employs shorting for charge recovery between each delivered stimulation pulse train (e.g., a series of 16 pulses over a short duration). Shorting refers to connecting each electrode contact 148 together. This may be accomplished, for example, by electrically connecting all the electrode contacts 148 together. By shorting the electrode contacts 148 between pulse trains, charge that has built up in the tissue may leave the tissue via the electrode contacts 148 and exit to other electrodes.

FIG. 3A illustrates two 20 ms pulse trains 302A and 302B. Each of these pulse trains 302A and 302B comprises a plurality of unbalanced bi-phasic pulses 304, where more negative charge flows into the electrode contact 148 than flows out of the electrode contact 148. Thus, over time a net negative charge builds up in the tissue.

FIG. 3B illustrates the charge flowing into and out of electrode contact 148 due to the pulse trains illustrated in FIG. 3A. As shown, a negative charge builds up in the tissue during the pulse train 302A. As noted above, in this example shorting is employed, thus during the time between the end of the first pulse train 302A and the start of the second pulse train 302B, the net negative charge built up in the tissue is dissipated. Then, during the second pulse train 302B, net negative charge again flows into the electrode contract 148, and so on.

Additionally, it has been recently discovered that unbalanced stimulation applied in cochlear implants employing high rate stimulation strategies can have perceptual as well as safety implications. The following described embodiments describe systems and methods that correct for charge imbalances. In describing these embodiments, an embodiment will first be described that does not employ separate in-series capacitors. This first embodiment may be helpful in reducing the safety concerns that may result from unbalanced stimulation. A second embodiment will then be described that provides a faster acting mechanism that corrects for charge imbalances. This second embodiment uses, preferably, in-series capacitors and may be helpful in reducing both safety concerns and reducing unwanted perceptual issues that may result from unbalanced stimulation. It will be understood that the aforementioned capacitors in this second embodiment are used to accurately measure the total charge delivered to an electrode, and that other alternative methods of accurately measuring the total charge delivered to an electrode may also be used. Such alternative methods include, but are not limited to, the use of accurate electronic charge measurement circuits with very low offset errors.

Figure 4:
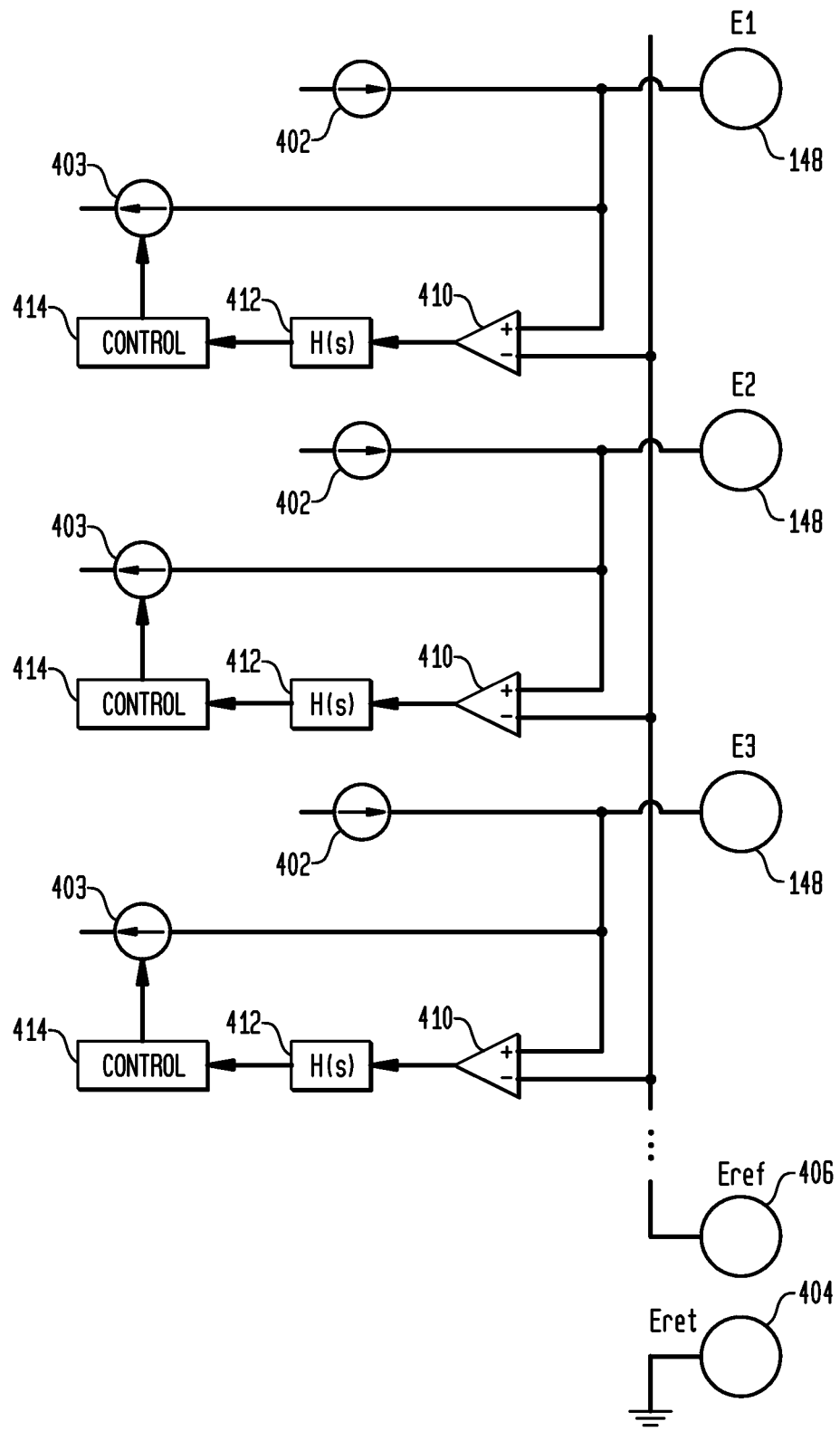
FIG. 4 illustrates a conceptual diagram of a stimulating medical device comprising a charge imbalance compensation system, in accordance with an embodiment.

FIG. 4 illustrates a conceptual diagram of a stimulating medical device comprising a charge imbalance compensation system, in accordance with an embodiment. This embodiment may be helpful in reducing safety concerns resulting from unbalanced stimulation. Although FIG. 4 is discussed below with reference to a cochlear implant, embodiments in accordance with the embodiment of FIG. 4 may be used in other embodiments in which electrical stimulation (neural or other electrical stimulation) is delivered within the body from either an implanted device, or an externally disposed device.

In FIG. 4, a plurality of electrode contacts 148 are arranged such, as discussed above with reference to FIG. 1, for providing electrical stimulation to a recipient of cochlear implant 100. In the embodiment of FIG. 4, the cochlear implant 100 is configured for application of monopolar stimulation in which cochlear implant 100 comprises an extra-cochlea return electrode 404. It should be, however, understood that in other embodiments other types of stimulation may be used, such as bipolar or tri-polar, type stimulation.

Figure 5:
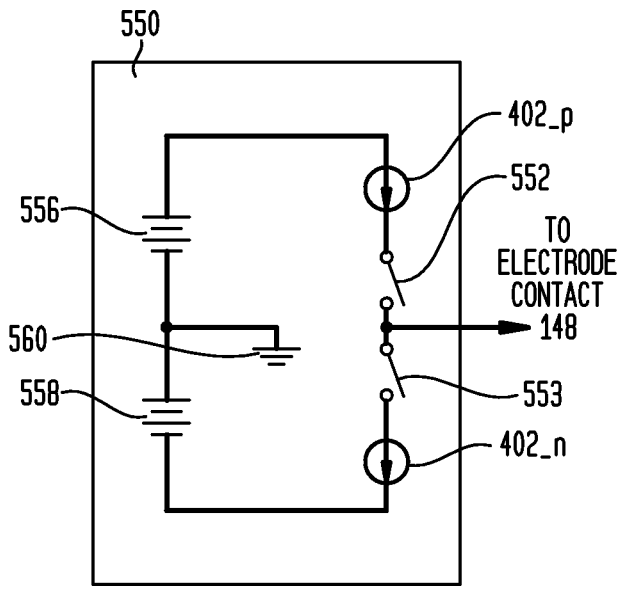
FIG. 5 illustrates a simple exemplary circuit that may be used for implementing a stimulation current source, in accordance with an embodiment.

As shown in FIG. 4, each electrode contact 148 is connected to a corresponding stimulation current source 402 and a compensation current source 403. FIG. 5 illustrates a simple exemplary circuit 550 that may be used for implementing stimulation current source 402, which in the presently described embodiment is configured to provide current for both the positive and negative phases of a bi-phasic pulse. As shown, a switch 552 is used to open and close a connection a between the electrode contract 148 and a positive voltage supply 556. Another switch 553 opens and closes a connection between the electrode contact 148 and a negative voltage supply 558. Each voltage supply may be grounded 560. In an embodiment, a control circuit, which is discussed in more detail below, may open and close switches 552 and 553 to provide the positive phase (illustrated by $402\_p$) and negative phase (illustrated by $402\_n$) of the bi-phasic pulses.

In the illustrated embodiment and as will discussed further below, the charge imbalance compensation system is configured to detect if a residual charge on an electrode contact 148 exceeds a threshold, and if so, direct that a corresponding compensatory current be applied. In the illustrated embodiment, the charge imbalance compensation system comprises a reference electrode 404, a differential amplifier 410, a filter 412, a control circuit 414, and a compensation current source 403.

Compensation current source 403 may operate independently of stimulation current source 402 and be used to provide a compensation charge via the electrode contacts 148 to help ensure that the charge delivered to the tissue stays within safe limits for the recipient. Compensation current source 403 may operate under the control of a control circuit 414 to source or sink charge via the electrode contacts 148 in helping ensure the charge remains within safe limits. The operation of compensation current source 403 and control circuit 414 will be discussed in more detail below.

As illustrated, a corresponding differential amplifier 410 is connected to each electrode contact 148 and the reference electrode 406. Each differential amplifier 410 determines and amplifies the potential difference between its corresponding electrode contact 148 and the reference electrode 406. The gain of the differential amplifier may be any appropriate value (e.g., 0.1, 1, 10, etc.) and depends on the specifics of the particular application in which the system of FIG. 4 is implemented. In the embodiment of FIG. 4, the same reference electrode 406 is used for all electrode contacts 148; however, in other embodiments one or a plurality of reference electrodes may be used.

Reference electrode 406 does not carry any stimulation in the presently described embodiment. Further, reference electrode 406 is in contact with the tissue or a bodily fluid of the recipient and provides a measurement of the recipient's tissue potential. For example, in an embodiment reference electrode 406 may be included in the stimulating assembly 118 disposed in the recipients cochlea. In such an embodiment, reference electrode 406 may be in contact with the perilymph within the cochlea in a similar manner to electrode contacts 148. In other embodiments, reference electrode 406 may be implanted external to the recipient's cochlea. For example, the reference electrode may be included in the stimulation assembly 118 but located along the stimulation assembly 118 such that the reference electrode 406 is located outside the cochlea after implantation of cochlear implant 100.

Further, in embodiments, reference electrode 406 is formed from the same material as electrode contacts 148 (e.g., platinum) such that the half-cell potential across each electrode contact 148 and reference electrode 406 is the same. The half-cell potential refers to the potential difference between an electrode contact and the tissue or body fluid (e.g., perilymph). In embodiments, reference electrode 406 may have a larger surface area than electrode contacts 148 (e.g., similar in size to the extracochlear return electrode 404), such that the impedance of the reference electrode 406 is relatively small. In an embodiment, reference electrode 406 may comprise a parallel combination of electrode contacts that are not used for applying stimulation. These electrode contacts may be located along the stimulating assembly 118 and in contact with the periiymph. Using such a parallel combination allows a plurality of smaller electrode contacts (e.g., similar or the same size as the stimulating electrode contacts) to be interconnected to effectively provide a larger electrode contact.

As shown in FIG. 4, each differential amplifier 410 provides its output to a corresponding filter 412. Filter 412 may be a low pass filter configured to have a corner frequency high enough to prevent the build-up of residual charge that may result in unsafe conditions for the recipient, but low enough so that the system does not detect false positives due to the stimulation pulses or stimulus artefacts. That is, filter 412 may have a corner frequency below the stimulation pulse rate, but sufficiently high enough to prevent unsafe conditions for the recipient.

As noted above, the pulse duration of the applied biphasic pulses may be between 10 and 100 microseconds in cochlear implants. The electrode voltage response to the applied stimulation current, however, may be much slower acting and have a duration in the range of 1 millisecond. Moreover, non-zero voltages in the electrode contact-tissue interface may persist for a longer period, but should not persist for more than about 100 milliseconds. As such, in an embodiment, the cutoff frequency of each filter 412 may be selected to have a value between 10 Hz-1 kHz (1/100 millisecond-1/1 millisecond). For example, in an embodiment, filter 412 may be a linear time invariant filter having a 12 dB/octave roll-off and a cutoff frequency of 15 Hz. However, in other embodiments filter 412 may have different specifications, such as, for example, each filter 412 may be a second or higher order filter having a programmable cutoff frequency of about 100 kHz. Filters 412 may be digital filters implemented by a processor, such as a non-linear processor. Or, in yet another embodiment, non-linear filters may be used, or a combination of linear and non-filters may be used. It should be understood that these values for filters 412 are appropriate for a standard cochlear implant; other devices or different designs may require different values. It should also be understood that there are many different implementations and designs for filters, and other types of filters may be used in the embodiment of FIG. 4.

Filters 412 output the filtered signal to a compensation control circuit 414 that determines if a charge imbalance exists. If so, control circuit 414 directs compensation current source 403 to provide or sink an appropriate amount of current to help ensure the charge within the tissue remains within safe limits.

Figure 6:
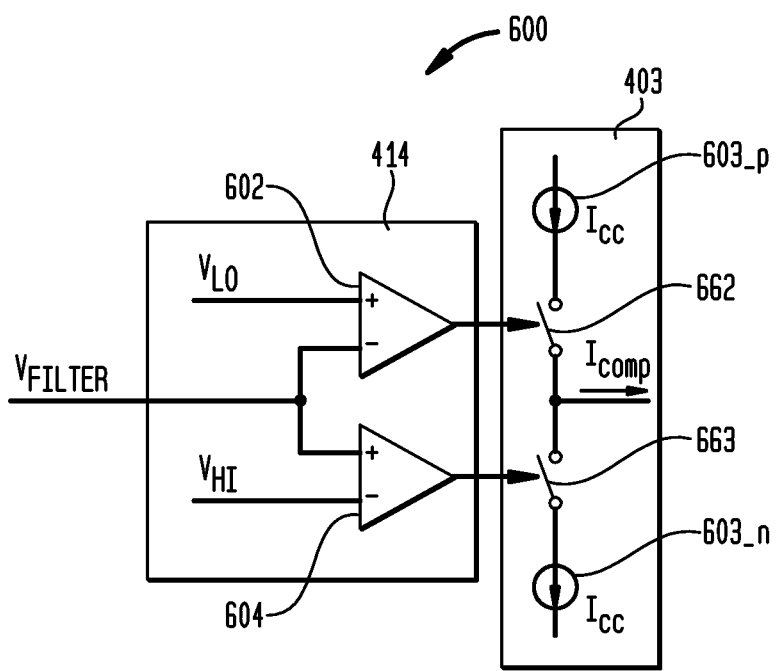
FIG. 6 illustrates an exemplary circuit that may be used for providing or sinking current if the residual charge on an electrode contact falls outside a safe window, in accordance with an embodiment.

In an embodiment, cochlear implant 100 may use a simple circuit that sinks or sources current via an electrode contact 148 if the cochlear implant 100 determines that the residual charge in the tissue exceeds a safe level. FIG. 6 illustrates an exemplary circuit 600 that may be used by control circuit 414 and compensation current source 403 for providing or sinking current if the residual charge on an electrode contact falls outside a safe window, in accordance with an embodiment. As illustrated, the output, $V_{filter}$, of the filter 412 is provided to both a lower limit comparator 602 and an upper limit comparator 604. Lower limit comparator 602 compares $V_{Filter}$ against a lower voltage limit, $V_{LO}$ (e.g., $V_{LO}$=-200 mV). If lower limit comparator 602 detects that $V_{Filter}$ falls below the minimum allowable voltage, $V_{LO}$, comparator 602 causes switch 662 to close and accordingly current from current source 603_p to be provided via electrode contact 148. In this example, the current is provided until $V_{Filter}$ is again within the safe window.

Similarly, upper limit comparator 604 compares $V_{filter}$ against an upper voltage limit, $V_{HI}$ (e.g., $V_{HI}$=220 mV). If $V_{Filter}$ is greater than $V_{HI}$, comparator 604 causes switch 663 to close and accordingly a current sink 603_n to sink from electrode contact 148. Thus, together the lower and upper voltage limits define a safe window, such that when the $W_{Filter}$ falls outside the safe window, a constant current, $I_{CC}$, is delivered to the electrode to return the voltage back to within the safe window.

The magnitude of the current, $I_{CC}$, delivered by compensation current source 403 may be selected so that it is larger than the largest expected stimulation DC current. For example, in an embodiment, the magnitude of the compensation currents is chosen such that the system can compensate for the largest expected error in the stimulation current. For example, if the maximum stimulation current is $I_M$=2 mA, the stimulation phase length is $T_P$=50 µs, the minimum stimulation period on a particular electrode is $T_{SP}$=500 µs, and the maximum stimulation current error is E=2% (typical numbers for cochlear implants), the worst-case DC current induced by the stimulation is $I_{DC}=I_M*T_P*E/T_{SP}$=4 µA. Thus, in an embodiment, the constant source compensation current, $I_{CC}$, may be selected to be 5 µA. Note that this magnitude is well below normal stimulation thresholds in cochlear implants and thus should not be perceptible to the recipient.

In another embodiment, rather than sourcing or sinking a current until $V_{Filter}$ returns to a level within the safe window, the control circuit 414 may simply provide or sink a current, $I_{CC}$, for a duration 1 millisecond in the event control circuit 414 determines that $V_{Filter}$ is outside the safe window. Then, after this 1 millisecond period, the control circuit 414 may re-sample $V_{Filter}$ to determine if it is within the safe window. If not, control circuit 414 may direct that a corresponding compensation current with a duration of 1 millisecond again be applied. That is, in this example, the control circuit 414 may synchronously sample the signal from filter 412 at 1 millisecond intervals in determining whether to apply a compensation current. In this embodiment, control circuit 414 may direct the compensation current source 403 to apply the compensation current during a dead period during which stimulation pulses for causing a hearing perception by the recipient are not applied.

Figure 7:
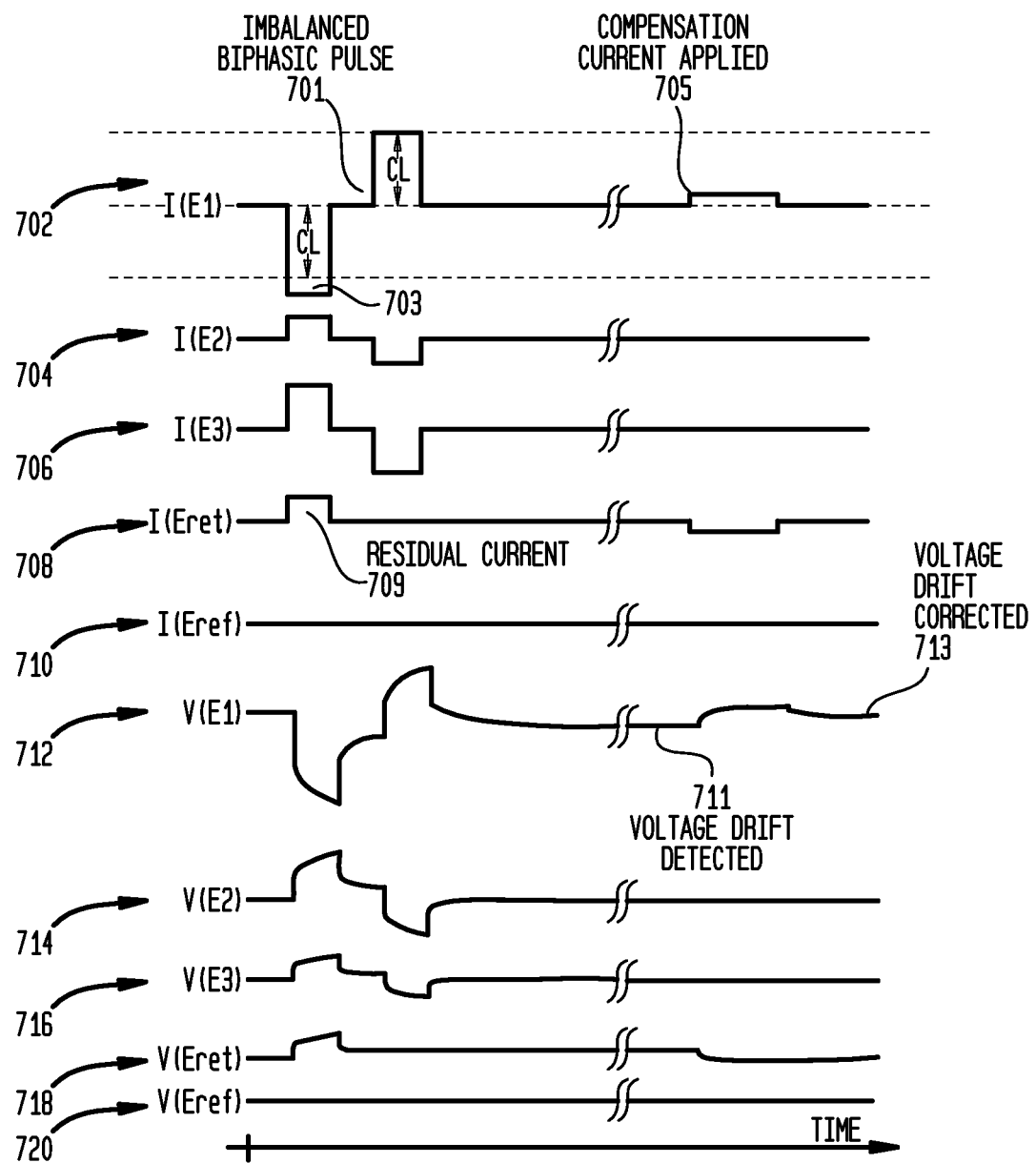
FIG. 7 provides an exemplary timing diagram illustrating the application of biphasic stimulation pulses in conjunction with a compensatory stimulation pulse, in accordance with an embodiment.

FIG. 7 provides an exemplary timing diagram illustrating the application of biphasic stimulation pulses in conjunction with a compensatory stimulation pulse, in accordance with an embodiment. As illustrated three stimulating signals 702, 704 and 706 are applied by three corresponding electrodes (E1, E2 and E3, respectively). Each of these stimulation signals comprises a biphasic current pulse. Also illustrated are the resulting currents on Eref 708 and Eref 710. As shown, the residual current 709 resulting from the biphasic pulses is received by Eref. Further, as shown by signal 710, no current is received by Eref in this example. The corresponding voltage on electrodes E1, E2, E3, Eref, and Eref is illustrated by voltage signals 712, 714, 716, 718, and 720, respectively.

As shown, the biphasic pulse 701 of stimulation signal 702 (E1) has a DC component 703 (nonzero net charge). As illustrated in voltage signal 712, this DC component 703 causes the voltage on the electrode V (E1) to build up. In an embodiment, this build up 711 is detected by the control system, which causes a compensation pulse 705 on E1 to be applied to lower the voltage and return the voltage 713 to within the safe window.

In another embodiment, rather than including a separate independent compensation source, cochlear implant 100 may correct for charge imbalances by adjusting the amount of charge provided or sunk by the current source 402, respectively, during the corresponding phase 204 or 206 (FIG. 2A) of the applied bi-phasic pulse 206. Referring back to FIG. 5, in an embodiment, control circuit 414 may compensate for the charge imbalance by adjusting the period of time switches 552 and 553 are closed. In such an embodiment, a separate compensation current source 403 may not be used.

In another embodiment, control circuit 414 may adjust the current levels of the currents sourced/sunk by current source 402, respectively rather than adjusting the durations of the pulse phases. Or, for example, control circuit 414 may adjust both the current levels and durations of the phases of the bi-phasic pulses.

Figure 8:
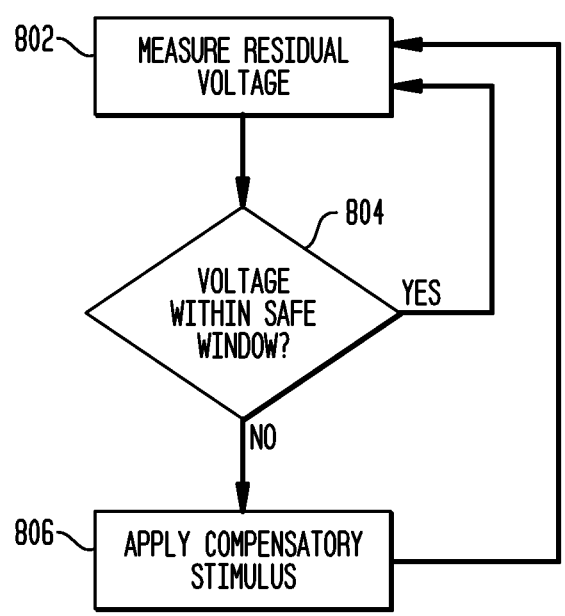
FIG. 8 is a high level flow chart illustrating a method for correcting for charge imbalances, in accordance with an embodiment.

FIG. 8 is a high level flow chart illustrating a method for correcting for charge imbalances, in accordance with an embodiment. FIG. 8 will be described with reference to the above-discussed FIG. 4. At block 802, differential amplifier 410 measures the residual charge remaining on its corresponding electrode contact 148. As noted above, differential amplifier 410 may measure this residual charge by comparing the potential of the electrode contact 148 and the potential of reference electrode 406. This measured voltage may also be low pass filtered to remove high frequency signals such as those resulting from a single phase of a biphasic pulse.

The filtered measured residual voltage is then provided to a control circuit 414 at block 804 that determines if the measured voltage (and accordingly the measured residual charge) is within a safe window as discussed above. If so, control is passed back to block 802 and the residual charge on the electrode contact 148 is continuously measured (e.g., at 1 millisecond intervals). If the residual charge (as represented by the residual voltage) is not within the safe window, control circuit 414, at block 806, causes a compensatory current to be applied to help correct for this error and bring the residual charge on the electrode contact 148 back to a value within the safe window. As noted above, various techniques may be employed for providing this compensatory current. For example, control circuit 414 may direct a dedicated independent compensatory current source 403 to apply a compensatory current to the electrode contact 148. Control circuit 414 may specify the timing, amplitude, and duration of the compensatory current to be applied by the compensatory current source. Or, in another embodiment, control circuit 414 may adjust the amplitude and/or duration of one or both phases of biphasic pulses applied by the stimulus current source 402 in providing stimulus for causing a hearing percept by the recipient. Or, for example, in other embodiments, other mechanisms may be used for providing a compensatory current to the electrode contact 148.

In stimulating medical devices, the electrode/tissue interface often exhibits a complex, non-linear impedance that varies significantly over time, from recipient to recipient, and from electrode to electrode. It may thus be difficult to a priori determine the optimum parameter set for the control system. It may therefore be helpful to acquire in-vivo data for system verification and/or determination of the specific parameters to be used for charge imbalance compensation.

In an embodiment, various parameters for the charge imbalance compensation system may be programmable such that they may be set and/or adjusted after implantation of the active implantable medical device. These parameters may include the cut-off frequency and filter order for filters 412, the magnitude of the compensation current ($I_{CC}$), the range of the safe window (e.g., the values of $V_{LO}$ and $V_{HI}$), and the sample rate for sampling $V_{Filter}$. For example, in an embodiment the filters 412 may be programmable to have a cutoff frequency of between 10 Hz-1 kHz and operate as a 1st, 2nd or 3rd order filter. Further, in an embodiment, the compensation current ($I_{CC}$) may be programmable to have a value between 100 nA and 10 µA. Further, the upper and lower limits of the safe window ($V_{LO}$ and $V_{HI}$) may be programmable in the range −400 mV to 400 mV.

Instead of using local current sources, filters, and control circuits for performing charge imbalance compensation on each electrode contact, in an embodiment, data can be passed to a microprocessor, such as a central digital signal processor (DSP) that controls charge imbalance compensation. This has the advantage that the compensation algorithm can be reprogrammed as more in-vivo data becomes available.

Figure 9:
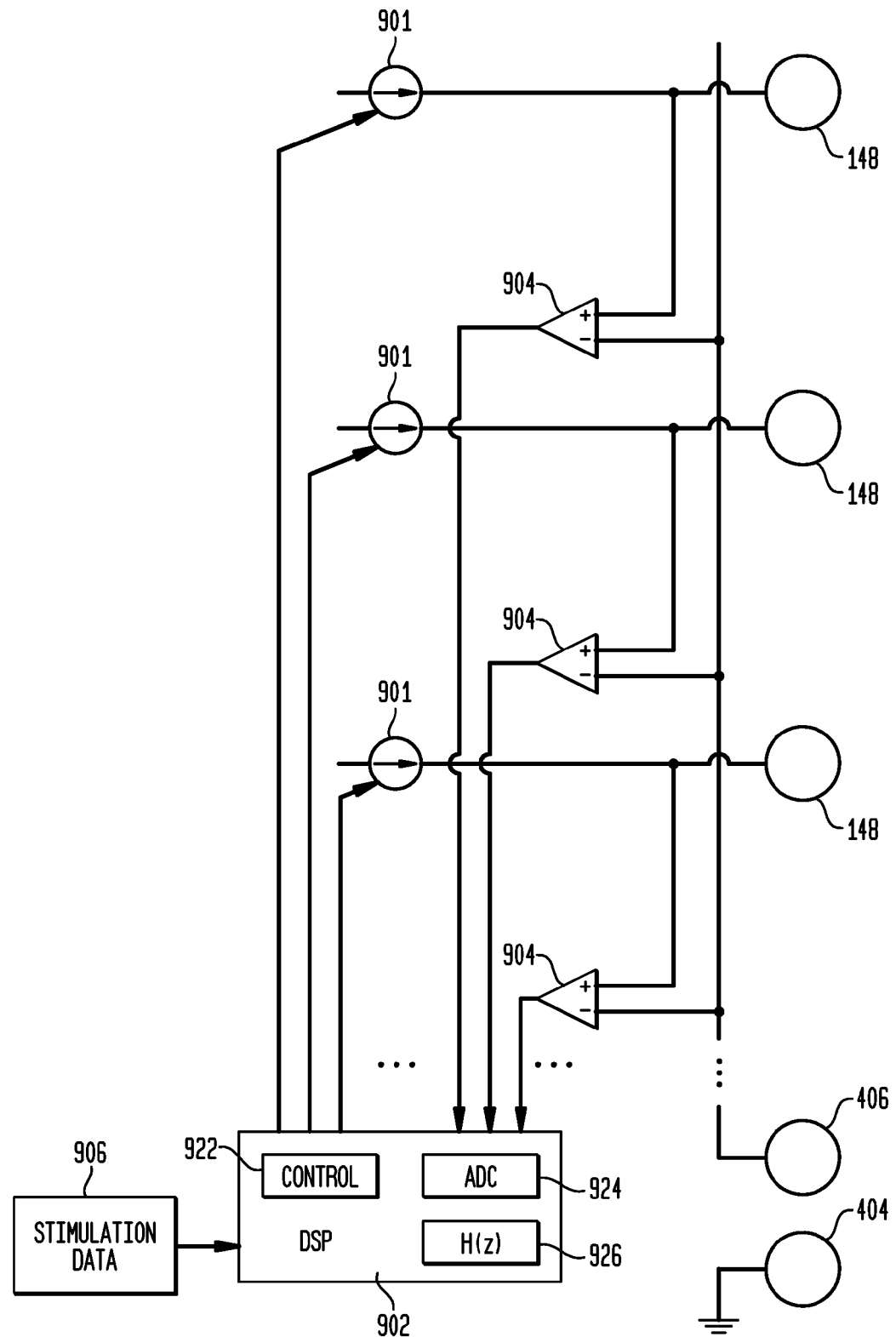
FIG. 9 illustrates an embodiment employing a DSP for charge imbalance compensation, in accordance with an embodiment.

FIG. 9 illustrates an embodiment employing a DSP for charge imbalance compensation, in accordance with an embodiment. As illustrated, system 900 comprises a DSP 902, a plurality of electrode contacts 148, a plurality of corresponding differential amplifiers 904, a plurality of corresponding current sources 901, and an extra-cochlea return electrode 404. DSP 902, differential amplifiers 904, and current sources 901 may be housed, for example, in stimulator unit 120 (FIG. 1) of cochlear implant 100.

As illustrated, DSP 902 receives stimulation data 906. This stimulation data 906 may be generated in sound processing unit 126 (FIG. 1) based on received sound signals and transmitted to DSP 902 of stimulator unit 120 (FIG. 1) via external transmitting unit 128 (FIG. 1) and internal receiving unit 132 (FIG. 1) as discussed above with reference to FIG. 1. A control module 922 of DSP 902 may then process the received stimulation data 906 to determine the stimulation pulses to be applied via electrode contracts 148. Control module 922 may then direct current sources 901 to apply stimulation in accordance with the received stimulation data 906 via the corresponding electrode contact 148.

As shown in FIG. 9 and as in the embodiment of FIG. 4, a differential amplifier 904 determines the difference between the potential of the corresponding electrode contact 148 and the reference electrode 406. In this embodiment, the difference is provided to DSP 902, which may digitize the received analog difference using an analog to digital converter (ADC) 924. The digitized difference may then be filtered using a digital filter, H(z), 926. The filtered signal is then passed to a control module 922 which determines whether compensation current is to be applied, and, if so, the direction and/or amplitude of the current to be applied. Control module 922 may function similar to the control circuit 414 discussed above with reference to FIG. 4. For example, in embodiments control module 922 may simply determine whether to apply compensation current and its direction, or, for example, control module may adjust the current level of the compensation current to be applied, may adjust the amount of time duration of one or more phases of the biphasic stimulation pulses, and/or the current level of these phases.

In the illustrated embodiment, control module 922 controls application of the compensation currents, not via separate dedicated current sources, but by perturbing the amplitudes of the phases of the biphasic pulses applied by the stimulation current sources 901 in applying stimulation in accordance with the received stimulation data 906. Accordingly in this embodiment the compensation current may be applied asynchronously without requiring a dead period between hearing percept stimulation pulses. It should be understood, however, that in other embodiments each electrode contact 148 may have a dedicated independent compensation current source that DSP 902 may control for application of appropriate compensation currents, which may be, for example, applied during a dead period in which hearing percept stimulation pulses are not applied. As used herein the term "hearing percept stimulation pulse" refers to a stimulation pulse, such as stimulation pulses 202 (FIGS. 2) and 701 (FIG. 1) intended to produce a hearing perception by the recipient.

In other embodiments, the system of FIG. 9 may be modified such that the performing electrode voltage sensing and filtering are provided individually for each electrode contact 148 and the resulting signals provided to a common DSP that controls application of the compensation currents. Or, in another embodiment, the DC voltages from the electrode contacts 148 and reference electrode 406 may be provided to the DSP and the above-discussed comparison provided by the DSP.

In another embodiment, the system may performing electrode voltage sensing, filtering and determination whether the electrode contact 148 is operating within the safe window individually for each electrode contact 148. A signal may then be passed to the DSP if the electrode contact 148 is found to be operating outside the safe window.

Or, in yet another embodiment, the control module or circuitry may direct the current sources (e.g., compensation or stimulation current sources) to use multiple (or a continuum) levels of compensation current depending on how large a difference there is between the potential of the electrode contact 148 and the reference electrode 406 (e.g., using larger compensation currents for higher voltage errors).

The above discussed embodiments of FIG. 4-8 may be helpful in reducing safety concerns arising due to unbalanced stimulation. However, in addition to safety concerns, perceptual problems may also result from unbalanced stimulation. The acceptable periods of time for charge imbalance to avoid unwanted percepts are shorter than those required for safety both in terms of response time and the extent of imbalance per pulse pair (both phases of a biphasic pulse). Therefore, the feedback circuit to avoid unwanted percepts needs to act quickly and accurately.

The response time to avoid unwanted percepts may depend on a number of factors, including the charge imbalance between the positive and negative phases of the biphasic pulse, the rate of pulse delivery, and the time constant of the nerve leakage, where the nerve fibers are modelled as leaky integrators. A typical response time in for a cochlear implant may be as short as 100 µs, where short, high rate pulses are used and the response time may be as long as several milliseconds for lower rate pulse trains. Further information on the response time of a human auditory nerve may be found, for example, in Zeng, F-G., et al., "Encoding Loudness by Electric Stimulation of the Auditory Nerve," NeuroReport 9, p. 1845-1848 (1998). Another factor in determining the response time for charge balance compensation to avoid unwanted percepts is the sensitivity of the recipient to charge imbalances, which varies from recipient to recipient and can be determined using psychophysical methods.

Figure 10:
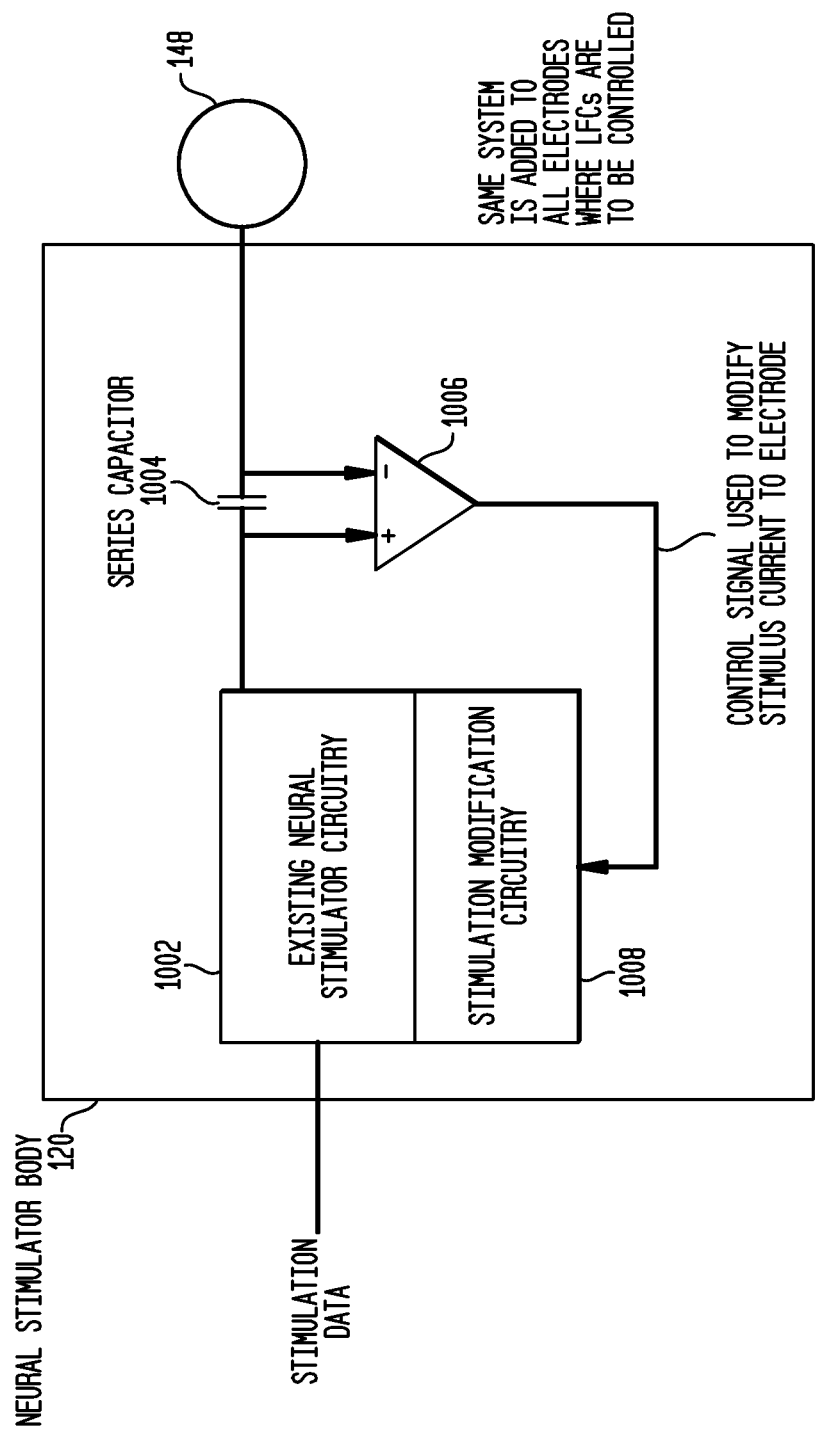
FIG. 10 illustrates a simplified diagram of a charge imbalance compensation system, in accordance with an embodiment.

FIG. 10 illustrates a simplified diagram of a charge imbalance compensation system, in accordance with an embodiment of the invention. In an embodiment, the illustrated system may be used for compensating for charge imbalances to reduce safety concerns and help avoid unwanted percepts due to charge imbalances. In the embodiment of FIG. 10, each electrode contact 148 receives stimulation signals from a stimulator unit 120, such as discussed above with reference to FIG. 1. For ease of explanation, FIG. 1 only illustrates the circuitry for a single electrode contact of stimulating assembly 118. It should, however, be understood that in embodiments each electrode contact 148 of stimulating assembly 118 may comprise similar circuitry for compensating for charge imbalances.

Stimulator unit 120 includes stimulation circuitry 1002 for generating stimulation signals (e.g., biphasic pulses) delivered by the electrode contacts 148. This stimulation circuitry may be similar to stimulation circuitry in existing cochlear implants and function to receive the stimulation data from sound processor 126 (e.g., via internal receiving unit 132) and generate stimulation signals such as was discussed above with reference to FIG. 1. As noted above, these stimulation signals may comprise biphasic pulses, such as, for example, a pulse train comprising a plurality of biphasic pulses. Stimulation circuitry 1002 may comprises hardware and software for generation of the stimulation signals. For example, stimulation circuitry may comprise a processor (e.g., a DSP, Integrated Circuit (IC), etc.) that executes software in converting the received stimulation data to stimulation signals.

As noted, in the embodiment of FIG. 10, stimulator unit 120 may comprise a charge imbalance compensation system. This system may be configured to detect if a residual charge on an electrode contact 148 exceeds a threshold, and if so, direct that a corresponding compensatory current be applied. In the illustrated embodiment, the charge imbalance compensation system comprises a capacitor 1004, a differential amplifier 1006, and stimulation modification circuitry 1008. It will be noted that the capacitor in the illustrated embodiment is used to provide an accurate measure of the total charge delivered to the electrode. In alternative embodiments the capacitor may be replaced with alternative forms of charge measuring device, such as accurate electronic charge measurement circuitry employing very low offset amplification.

As illustrated, capacitor 1004 is placed is series with each electrode contact 148. Many neural stimulators already include these capacitors in series with electrode contacts 148. The voltage across the terminals of capacitor 1004 provides an accurate representation of the integral of the charge flow to electrode contact 148, and accordingly provides a measure of the residual charge on the electrode contact 148. In an embodiment, capacitor 1004 may be a low leakage capacitor with a small capacitance (e.g., 1.0 µF).

Each side of capacitor 1004 is input to a differential amplifier 1006, which outputs an amplified difference between the potentials on each side of capacitor 1004. In other words, differential amplifier 1006 provides an amplified version of the voltage across the terminals of capacitor 1004. Differential amplifier 1006 may be a high impedance differential amplifier having a gain (i.e., amplification) of any value (e.g., 0.1, 1, 10, etc.) appropriate for the specifics of the system in which the system of FIG. 10 is implemented. The signal output from differential amplifier 1006 is representative of the total charge flow as measured across the capacitor. Or, in other words, the signal output from differential amplifier 1006 provides a measurement of the net charge flow into the electrode contact 148.

As shown, differential amplifier 1006 provides the amplified difference to stimulation modification circuitry 1008. Stimulation modification circuitry 1008 may comprise hardware and/or software configured to modify the stimulation signals provided by stimulation circuitry 1002. For example, stimulation modification circuitry 1008 may direct stimulation circuitry 1002 to change the amplitude and/or duration of one or more phases of the biphasic pulses stimulation. The amount and type of modification to the biphasic pulses may depend on the amount and sign of the signal received from differential amplifier 1006.

In an embodiment, stimulation modification circuitry 1008 may implement a simple algorithm in which stimulation modification circuitry 1008 adjusts the duration of the positive phase of the biphasic pulse by a correction factor that is proportional to the signal received from differential amplifier 1006. The correction factor may be chosen such that the total imbalanced charge flow will not exceed the perceptible limit. By adjusting the amount of charge provided during a particular phase(s) of the biphasic pulse, stimulation modification circuitry may effect the application of a compensation current. That is, the additional charge (or reduction in charge) determined by the stimulation modification circuitry provides a compensation current flowing in a particular direction that is provided simultaneous with the application of the charge from the biphasic stimulation pulses.

This compensation current provided to electrode contact 148 modifies the total current flowing through the electrode contact to cancel out any (within an acceptable margin) residual charge remaining on the electrode contact 148. Stimulation modification circuit 1008 may adjust the provided compensation current so that the charge imbalance falls below the perceptible limit, or within an acceptable margin of the perceptible limit (i.e., below a threshold). A description of an exemplary method for determining the perceptible limit will be described below with reference to FIG. 12.

Figure 11:
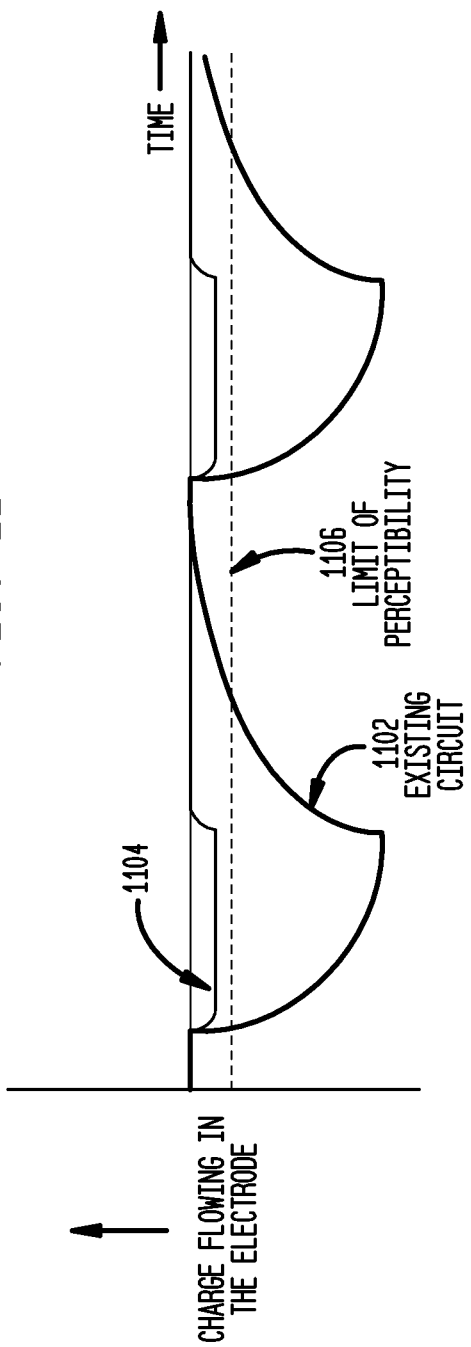
FIG. 11 illustrates charge flowing through an electrode contact due to the stimulation signal with and without a compensatory current, in accordance with an embodiment.

FIG. 11 illustrates charge flowing through an electrode contact 148 due to the stimulation signal with and without a compensatory current, in accordance with an embodiment of the invention. FIG. 11 illustrates the charge 1102 resulting from the stimulation signal without using compensatory current, and the charge 1104 resulting when a compensatory current is used, such as described above with reference to FIG. 10. For clarity, the charge resulting from individual pulses of the stimulation signal is not illustrated (i.e., the charge resulting from the individual pulses illustrated in the above discussed FIG. 3B). As shown, the charge 1102 from the stimulation signal exceeds the perceptible limit 1106 when a compensatory current is not use. However, when a compensatory current is used, such as described above with reference to FIG. 10, the resulting charge does not exceed the perceptible limit 1106. Further, as shown, the response time (i.e., how quickly the charge returns to zero) is faster in the system employing a compensatory current than the system in which it is not used.

Additionally, as illustrated by charge 1102, a charge imbalance between phases of a bi-phasic pulse may result in the residual charge quickly exceeding the perceptible limit (e.g., within a few pulses of a pulse train). As such, in an embodiment, it may be desirable for the charge imbalance compensation system (e.g., capacitor 1004, differential amplifier 1006, and stimulation modification circuitry 1008) to be fast acting. For example, it may be desirable the charge imbalance compensation system be capable of detecting a charge imbalance and applying the compensatory current within the time period equal to or less than the duration of a few stimulation pulses (e.g., 2-5 stimulation pulses). Because the residual charge that may cause percept issues is lower than the residual charge that may give rise to safety concerns, the charge imbalance compensation system for reducing perceptual issues may be designed to be much faster acting than a system concerned solely with safety.

As noted above, in an embodiment, a series capacitor 1004 and differential amplifier 1006 would be included on every electrode contact 148. In other embodiments, rather than having a series capacitor and differential amplifier for each electrode, a series capacitor and differential amplifier might be used on only a subset of electrode contacts 148. This may be beneficial in systems in which there are size limitations or concerns. For example, in a cochlear implant system using monopolar stimulation, it might be sufficient to only include the series electrode and differential amplifier on the return electrode. In other words, in an embodiment employing monopolar stimulation, a mechanism such as described in FIG. 10 may only be used to provide compensatory stimulation on the monopolar electrode. Additionally, embodiments such as described above with reference to FIG. 10 may be implemented in stimulating medical devices providing either asynchronous or synchronous stimulation.

In another embodiment, the stimulation modification circuitry 1008 may sample the signal from the differential amplifier 1006 at a time when it knows that no stimulus current is flowing through the electrode contact. This information may be provided to stimulation modification circuitry 1008 by the stimulation circuitry 1002. Or, in an embodiment, if current is always flowing through the electrode contact 148, such as in an analog stimulation strategy, then stimulation modification circuitry 1008 may sample the signal from the differential amplifier 1006 when the nominal charge imbalance is zero. By sampling at these points the effect of the stimulation pulse itself can be ignored since it will be nominally zero between pulses. Such systems may be useful in systems in which relatively large stimulus charges are flowing through the electrode contact.

In yet another embodiment, a low pass filter may be employed between the differential amplifier 1006 and the stimulation modification circuitry 1008. This low pass filter may be similar to the low pass filters 410 discussed above with reference to FIG. 4. Because perception issues can occur more rapidly than safety concerns, the cut-off frequency of the low pass filter used in a system to control percept issues may have a higher cutoff frequency than those discussed above with reference to FIG. 4. In an embodiment, the cutoff frequency of the low pass filters may be selected to be lower than the frequency of the stimulus signal and higher than the frequency required to prevent perception of the charge imbalances.

In the embodiment of FIG. 10, a reference electrode such as discussed above with reference to FIG. 4 is not included. It should be noted, however, that in the above described embodiment of FIG. 4, the combination of the electrode contact 148 and the tissue or body fluid (e.g., perilymph) can be viewed as functioning as a series capacitor. For example, when an electrode contact 148 is placed in perilymph, a thin layer of water molecules may form on the surface of the electrode contact 148, which as noted above may be manufactured from platinum. This combination of the surface of the electrode contact 148, the thin layer of water molecules, and the perilymph can be viewed as functioning as a capacitor in series with the electrode contact 148. Further, in such an embodiment, the measured potential of the electrode contact 148 has the effect of measuring the potential on the metal side of this capacitor. The reference electrode 406, which may also be located in the periiymph, has the effect of measuring the potential on the metal side of a similar, unstimulated capacitor. Thus, the signals provided to the differential amplifier 410 of FIG. 4 can be viewed as providing the voltage stored across this in-series capacitor created at the metal/tissue surface of electrode 148. This voltage across this in-series capacitor thus provides a measure of the net charge flowing into the electrode contact.

Because the "capacitor" resulting from a combination of the electrode contact 148, thin layer of water, and the perilymph, the tolerances for this capacitor are not as easily controlled and can vary from electrode contact to electrode contact and over time. As a result, measurement of this voltage difference may be sufficient in systems in which safety is the principal concern. However, in faster acting systems, such as when trying to control percept issues in systems with high pulse rates, a system such as illustrated in FIG. 10 may provide better results due to the ability to use capacitors in which the capacitor specifications may be more precise and not vary significantly over time.

Figure 12:
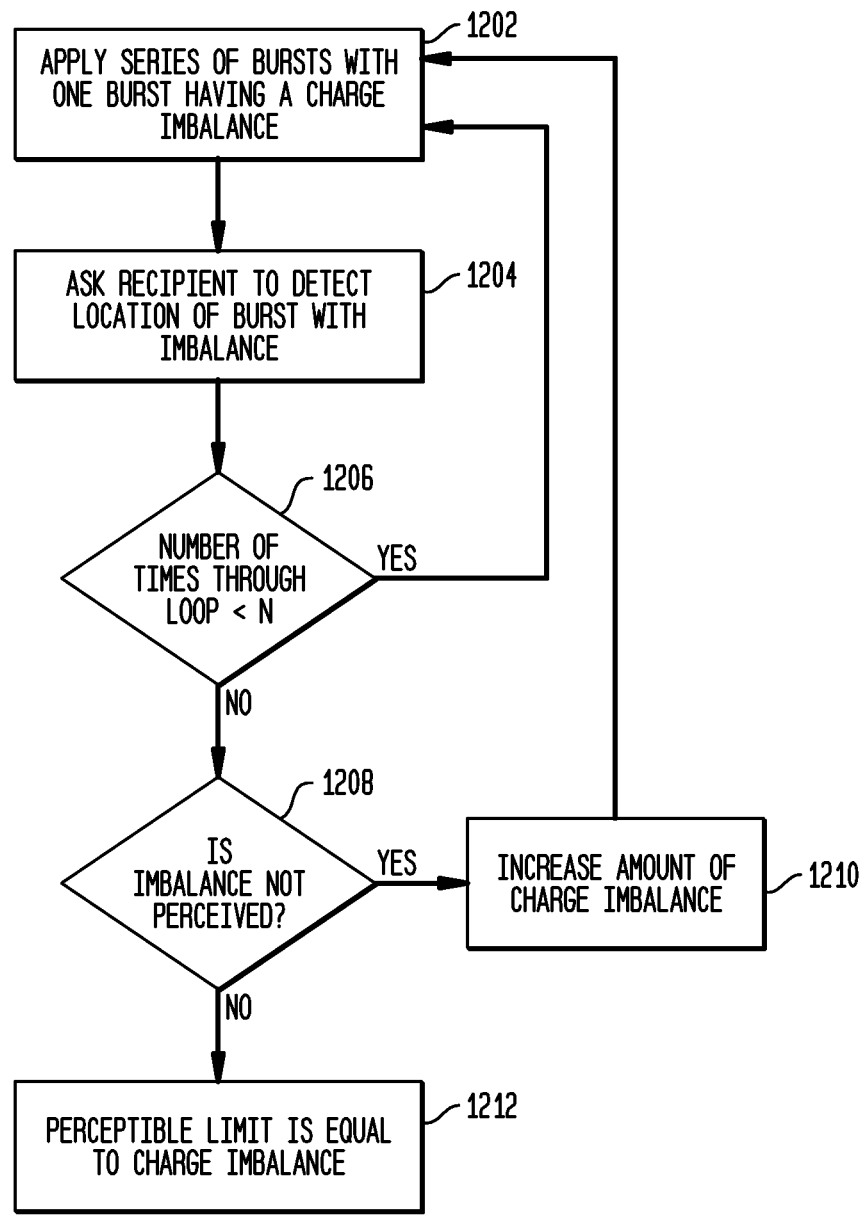
FIG. 12 is a flow chart of an exemplary method for determining the perceptible limit, in accordance with an embodiment.

FIG. 12 is a flow chart of an exemplary method for determining the perceptible limit, in accordance with an embodiment of the invention. At block 1202, the recipient is presented with a series of bursts of biphasic stimulation pulses on a particular electrode. One of the stimulus bursts includes a deliberately induced charge imbalance that is different than the other bursts in the series. The particular burst with charge imbalance may be randomly selected. During the initial pass through block 1202 the amount of charge imbalance may be initially set low.

An audiologist using a fitting system connected to cochlear implant 100 may specify the size of the initial charge imbalance. Fitting system 1202 may be, for example, a computer with a display that may present a graphical user interface (GUI) to the audiologist. Using this GUI, the audiologist may specify the size of the charge imbalance as well as the number of bursts to be provided and when the series of bursts are provided, as well as other parameters, such as the specifics of the stimulation burst presented to the recipient via cochlear implant 100. The location of the burst with the charge imbalance may be randomly selected by the fitting system and its location displayed to the audiologist via the GUI, or, for example, the audiologist may specify the location of the burst with the charge imbalance using the GUI.

The audiologist then asks the recipient to pick which burst in the series is perceptually different at block 1204. This process is then repeated a number, N, times with the location of the burst with the imbalance randomly, for example, selected during each pass. Thus, if at decision 1206 the number of times through the loop is less than N, the process returns to block 1202. If, however, the number of times through the loop is equal to N, the process passes to block 1208.

After the loop comprising blocks 1202 and 1204 is passed through N times, at decision 1210, the audiologist determines whether the recipient correctly identified the location of the burst with the charge imbalance a particular number of times (e.g., the location was correctly identified 80% of the time). Or, for example, at block 1204, the audiologist may, using the GUI, identify whether or not the recipient correctly identified the location of the burst with the charge imbalance. Then, at block 1200, the fitting system determines if the location of burst with the imbalance was correctly identified the particular number of times.

If at block 1210, it is determined that the charge imbalance is not perceived (e.g., it was not correctly located a sufficient number of times), the size of the charge imbalance is increased and the process returned to block 1202.

If at block 1210, it is determine the charge imbalance is perceived, the process determines at block 1212 that the perceptible limit is equal to the size of the charge imbalance during the most recent pass through blocks 1202 and 1204.

The embodiment of FIG. 12 is but one example of a method for determining the perceptible limit of the charge imbalance, and in other embodiments, other methods may be used for determining the perceptible limit. For example, in an embodiment, the charge imbalance may be increased by a particular step size at block 1210 and then when the charge imbalance is deemed perceived the step size is reduced and the charge imbalance is then reduced during each pass through the loop until the charge imbalance is not detected. Then, the step size is further reduced and the charge imbalance increased until the charge imbalance is again perceived. Such, a mechanism may be used to further refine the size of the perceptible limit. Or, for example, certain of the steps discussed above with reference to FIG. 12 may be performed by the audiologist or a different type of system may be used for determining the perceptible limit of the charge imbalance.

Or, in yet another embodiment, the perceptible limit may be determined for each of a population of recipients, to determine the mean and standard deviation for the perceptible limit across the population. Then, this mean and standard deviation can be used when setting the perceptible limit for all recipients to avoid determining the perceptible limit individually for each recipient.

As noted, while the embodiment of FIG. 10 was discussed with reference to a cochlear implant, embodiments may also be implemented in other active implantable medical devices, such as neural stimulators where perceptual issues may arise.

In an embodiments, the faster-acting mechanism discussed above with reference to FIGS. 10-12 for controlling percepts may be combined with the mechanism discussed above with reference to FIGS. 4-9 for helping improve safety of the system. This may be beneficial because the safety loop (e.g., the mechanisms discussed above with reference to FIGS. 4-9) may provide a back-up in case of failure of the perceptual loop (e.g., the mechanisms discussed above with reference to FIG. 10). Additionally, such a combined system may allow the perceptual loop (e.g., (e.g., the mechanisms discussed above with reference to FIG. 10) to be designed with lower current driving capacity, which may make the design more power and space efficient. Limiting the maximum amplitude of the feedback in the perceptual loop may also help prevent the fast acting loop from oscillating due to positive feedback. For stimulation modification circuitry 1008 may only be able to modify the current levels or durations within a range specified by a maximum and minimum adjustment, or, if a separate compensatory current source is used, it may be designed with more limited current driving capacity. For example, most of the time the perceptual loop may be making small fast corrections to the applied stimulation to avoid perception of any charge imbalance and thus a current source with a large driving current need not be used. However, should the limited current drive capability of the perceptual loop be unable to adequately correct for the charge imbalance, the safety loop (which may sample the voltages at a much slower rate) can provide adequate current corrections in the event a safety issue arises.

Figure 13:
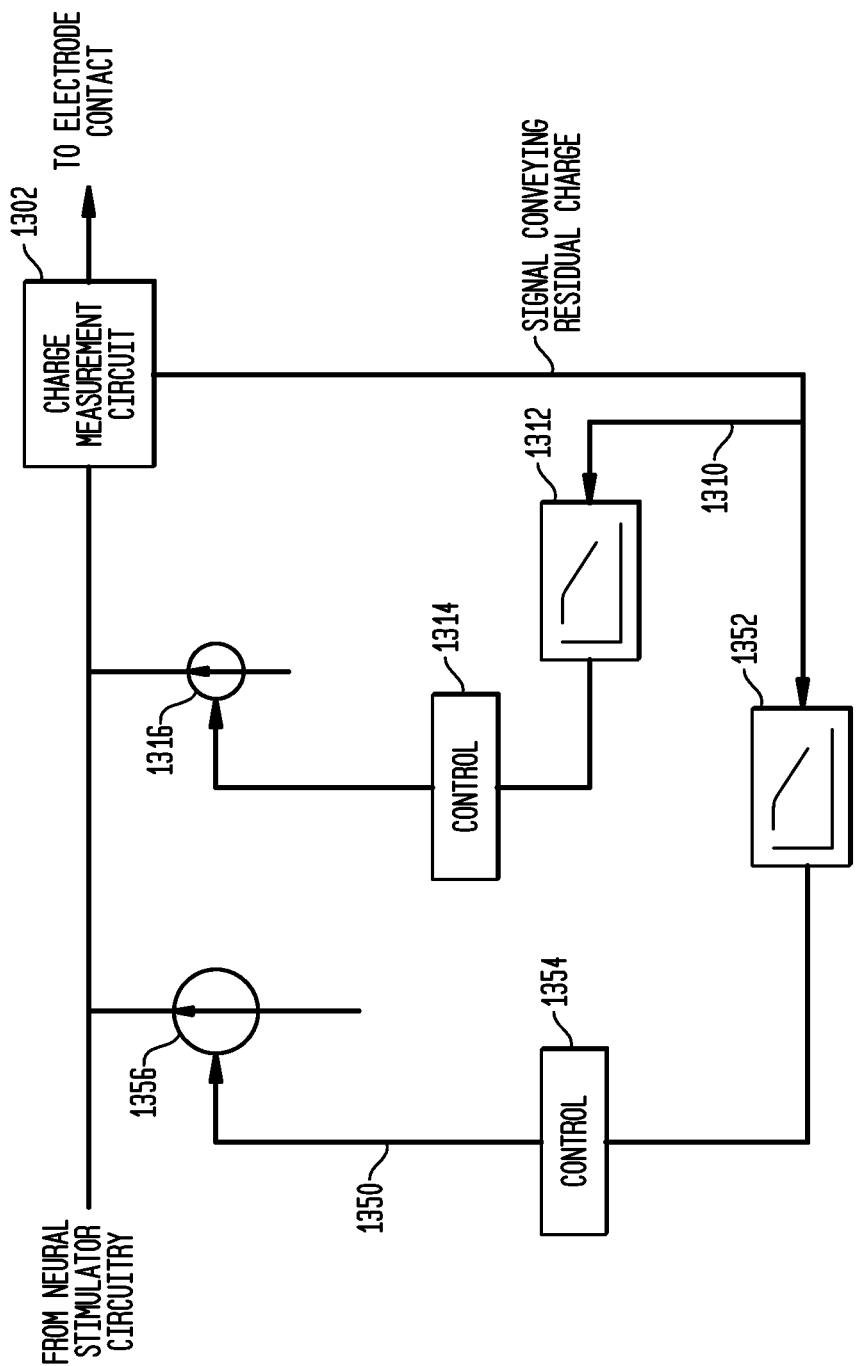
FIG. 13 provides a simplified conceptual diagram of a dual loop charge imbalance compensation system that combines a slower safety loop with a faster acting perceptual loop, in accordance with an embodiment.

FIG. 13 provides a simplified conceptual diagram of a dual loop charge imbalance compensation system that combines a slower safety loop with a faster acting perceptual loop, in accordance with an embodiment of the invention. As illustrate dual loop charge control system 1300 comprises an inner perceptual loop 1310 and an outer safety control loop 1352. This system 1300 may be used in a system similar to that illustrated in FIG. 4 where a stimulation current source(s) (e.g., 402 of FIG. 4) provides stimulation current to the electrode contact(s).

As illustrated, the inner faster-acting perceptual loop 1310 comprises a low-pass filter 1312, a control circuit 1314, and a small current source 1316. The filter 1312 may receive as an input a measure of the residual charge received from a charge measurement circuit 1302. The cutoff frequency of the low-pass filter 1312 may be, for example, in the range of 100 Hz to 5 kHz. The filter 1312 provides the filtered measure of the residual charge to control circuit 1314. The control circuitry 1314 may operate similarly to the control circuitry 414 discussed above with reference to FIG. 4 to apply a corresponding compensatory current using current source 1316. Since perceptual loop 1310 is faster acting with the corresponding possibility of instability, the current source 1316 may be configured to only apply a small compensation current that is sufficient to control perceptual effects in a normally functioning implant due to phase imbalance between the phases of the bi-phasic pulse.

The outer safety loop 1350 comprises a low-pass filter 1352, a control circuit 1354, and a small current source 1356. The filter 1352 may also receive as an input a measure of the residual charge received from charge measurement circuit 1302. The cutoff frequency of the low-pass filter 1352 may be, for example, in the range of 20 mHz to 10 Hz. The filter 1352 provides the filtered measure of the residual charge to control circuit 1354. The control circuitry 1354 may operate similar to the control circuitry 414 discussed above with reference to FIG. 4 to apply a corresponding compensatory current using the larger current source 1356. The safety loop 1350 in this example is configured to ensure the system operates safely. As such, in the present embodiment, the safety loop is configured to respond to a potentially faulty system where, for example, one entire phase of the biphasic pulse may be missing. Thus, the safety loop 1350 is configured to be able to provide large currents (e.g., as large as the stimulation current). Further, the safety loop 1350 may be slower acting (e.g., cut-off frequency of filter 1352 in the range of 2 mHz to 10 Hz) since electrochemical by-products produced by unbalanced stimulation will takes some seconds to diffuse from the electrode contacts to the neural elements where it can cause damage.

For ease of explanation, the embodiment of FIG. 13 uses separate current sources 1316 and 1356 to deliver the compensation currents. In an alternative implementation, the charge imbalance compensation system may be configured to adjust either the pulse width or current level of one or more phases of the bi-phasic pulses.

Figure 14:
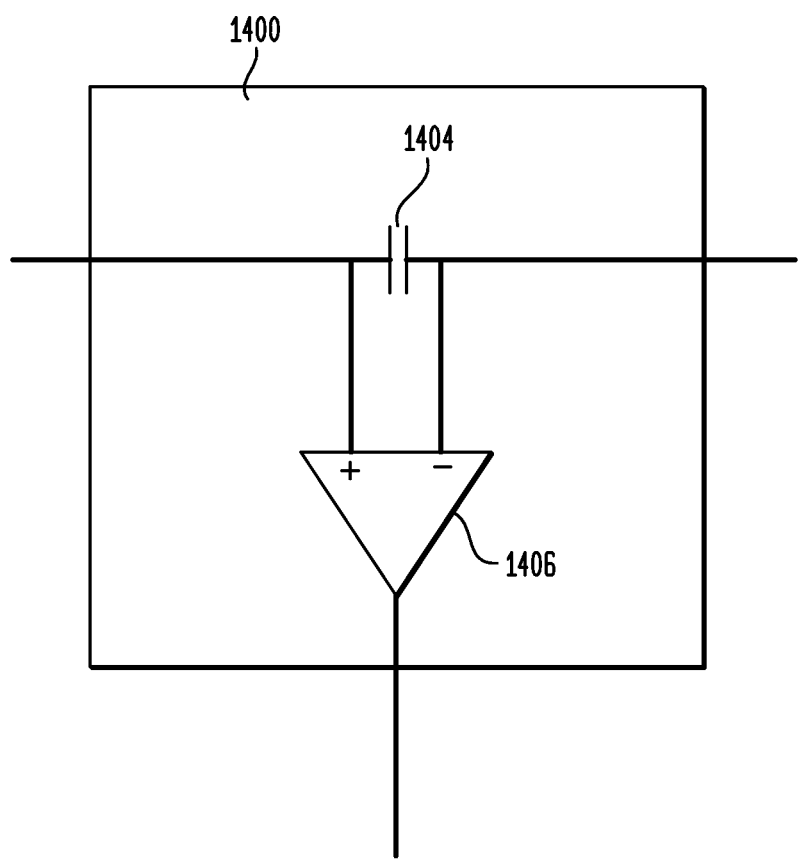
FIG. 14 provides a simplified schematic diagram of a charge measurement circuit, in accordance with an embodiment.

FIG. 14 provides a simplified schematic diagram of a charge measurement circuit, in accordance with an embodiment. This charge measurement circuit 1400 may be used as charge measurement circuit 1302 (FIG. 13). As illustrated, charge measurement circuit 1400 comprises a capacitor 1404 and a differential amplifier 1406. Charge measurement circuit 1400 may operate similarly to the charge measurement circuit of FIG. 10 comprising capacitor 1004 and differential amplifier 1006. It should be noted that this is but one example of a charge measurement circuit and in embodiments other circuits may be used, such as for example, a circuit employing an alternative to capacitor 1404 that may, for example, occupy less space within the implant housing.

All documents, patents, journal articles and other materials cited in the present application are hereby incorporated by reference.

Embodiments of the present invention have been described with reference to several aspects of the present invention. It would be appreciated that embodiments described in the context of one aspect may be used in other aspects without departing from the scope of the present invention.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart there from.

What is claimed is:

1. A method of controlling voltage in a stimulating medical device having a plurality of electrode contacts implanted in a recipient for delivering stimulation to the recipient, the method comprising:
   measuring a residual charge associated with an implanted electrode contact of the plurality of implanted electrode contacts;
   determining if the measured residual charge exceeds a threshold; and
   applying a compensation current if the measured residual charge exceeds the threshold.

2. The method of claim 1, further comprising:
   applying stimulation on the implanted electrode contact of the plurality of implanted electrode contacts by applying a biphasic pulse via the implanted electrode contact, wherein the biphasic pulse comprises a first phase and a second phase of opposite polarity from the first phase; and
   wherein the residual charge results from a charge imbalance between the first and second phases.

3. The method of claim 2, wherein applying a compensation current comprises:
   applying a current using a current source separate from a current source for delivering stimulation.

4. The method of claim 2, wherein applying a compensation current comprises:
   adjusting a pulse duration or amplitude of at least one phase of the biphasic pulse.

5. The method of claim 1, further comprising:
   low pass filtering the measured residual charge.

6. The method of claim 5, wherein the low pass filter has a cutoff frequency that is less than a pulse rate of the applied stimulation.

7. The method of claim 1, wherein measuring the residual charge comprises:
   measuring a voltage across a capacitor in series with the implanted electrode contact.

8. The method of claim 7, wherein the threshold is equal to or below a perceptible limit indicative of a current imbalance perceptible to the recipient.

9. The method of claim 1, wherein the stimulating medical device is a cochlear implant.

10. A stimulating medical device for delivering stimulation to a recipient, the stimulating medical device comprising:
    at least one implantable electrode contact configured to be implanted in the recipient and to deliver stimulation to the recipient;
    a current source configured to provide a stimulation current to the at least one implantable electrode contact;
    a charge imbalance compensation system configured to measure a residual charge associated with at least one of the implantable electrode contacts;
    determine if the measured residual charge exceeds a threshold; and
    direct that a compensation current be applied if the measured residual charge exceeds the threshold.

11. The stimulating medical device of claim 10, the charge imbalance compensation system comprises:
    a circuit configured to determine if the measured residual charge falls outside a predetermined range defined by first threshold and a second threshold; and
    wherein the charge imbalance compensation system is configured to direct that a compensation current be applied if the measured residual charge falls outside the predetermined range.

12. The stimulating medical device of claim 10, further comprising:
    a stimulation current source configured to apply stimulation on at least one of the implantable electrode contacts by applying a biphasic pulse via the implantable electrode contact, wherein the biphasic pulse comprises a first phase and a second phase of opposite polarity from the first phase; and
    wherein the residual charge results from a charge imbalance between the first and second phases.

13. The stimulating medical device of claim 12, further comprising
a compensation current source configured to apply the compensation current.

14. The stimulating medical device of claim 12, wherein the charge imbalance compensation system in applying a compensation current is configured to cause the stimulation current source to adjust a pulse duration or amplitude of at least one phase of the biphasic pulse.

15. The stimulating medical device of claim 10, further comprising:
a reference electrode configured to be positioned in body fluid or tissue of the recipient; and
a differential amplifier configured to measure a potential difference between the implantable electrode contact and the reference electrode.

16. The stimulating medical device of claim 10, further comprising:
a low pass filter configured to low pass filter the measured residual charge.

17. The stimulating medical device of claim 16, wherein the low pass filter has a cutoff frequency that is less than a pulse rate of the stimulation to be applied by the stimulating medical device.

18. The stimulating medical device of claim 17, wherein the threshold is equal to or below a perceptible limit indicative of a current imbalance perceptible to the recipient.

19. The stimulating medical device of claim 10, further comprising:
a capacitor in series with at least one of the implantable electrode contacts; and
wherein the charge imbalance compensation system is configured to measure the voltage across the capacitor.

20. The stimulating medical device of claim 10, wherein the stimulating medical device is a cochlear implant.

21. A method comprising:
measuring a voltage across a capacitor in series with an electrode contact;
determining if the measured voltage exceeds a threshold; and
applying a compensation current if the measured voltage exceeds the threshold.

22. The method of, claim 21, wherein determining if the measured voltage exceeds a threshold comprises
determining if the measured voltage falls outside a predetermined range defined by a first threshold and a second threshold, and
wherein applying a compensation current comprises applying a compensation current if the measured residual charge falls outside the predetermined range.

23. The method of claim 21, wherein measuring the voltage comprises:
measuring a potential difference between the electrode contact and a reference electrode, wherein the reference electrode is in contact with body tissue or body fluid of a recipient, and wherein current resulting from stimulation applied to the recipient does not flow through the reference electrode.

* * * * *